United States Patent [19]

Yurugi et al.

[11] 4,017,490
[45] * Apr. 12, 1977

[54] PYRIDO (3,4-d)PYRIDAZINES

[75] Inventors: Shojiro Yurugi, Kyoto; Shintaro Kikuchi, Takarazuka, both of Japan

[73] Assignee: Takeda Chemical Industries, Ltd., Osaka, Japan

[ * ] Notice: The portion of the term of this patent subsequent to Apr. 6, 1993, has been disclaimed.

[22] Filed: Aug. 21, 1975

[21] Appl. No.: 606,607

[30] Foreign Application Priority Data

Sept. 17, 1974 Japan .................... 49-107279

[52] U.S. Cl. .................. 260/246 B; 260/250 AC; 424/248.57
[51] Int. Cl.² ..................................... C07D 413/14
[58] Field of Search .............. 260/246 B, 250 A

[56] References Cited

UNITED STATES PATENTS 3,037,022  5/1962  Lowrie ................... 260/250 A
3,948,908  4/1976  Yurugi et al. ........... 260/246 B

OTHER PUBLICATIONS

Yurugi; Shojiro, et al. Chemical Abstracts vol. 78, 43400h, (1973).
Yurugi; Shojiro, et al. Chemical Abstracts vol. 78, 43402k, (1973).
Yurugi; Shojiro, et al. Chemical Abstracts vol. 79, 78,830w, (1973).

*Primary Examiner*—Donald G. Daus
*Assistant Examiner*—Jose Tovar
*Attorney, Agent, or Firm*—Wenderoth, Lind & Ponack

[57] ABSTRACT

Novel pyrido (3,4-d) pyridazines shown by the general formula:

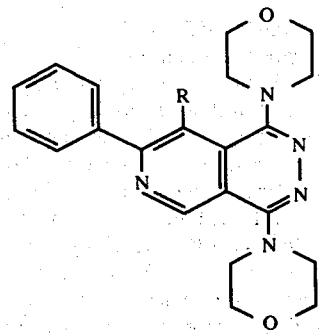

wherein R is a lower alkoxy group or a halogen atom and their pharmaceutically acceptable salts are excellent in diuretic properties, and are useful to human therapy of edema and hypertension.

1 Claim, No Drawings

PYRIDO(3,4-d)PYRIDAZINES

The present invention relates to novel pyrido[3,4-d]-pyridazines. More concretely, the present invention relates to novel pyrido[3,4-d]pyridazines of the general formula (I):

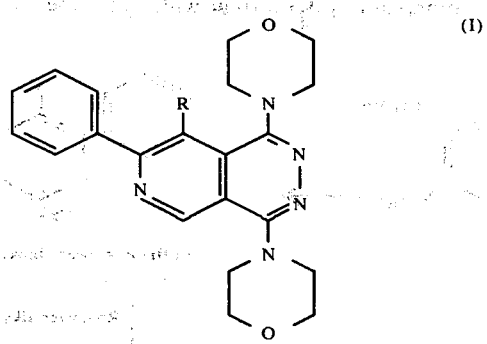

wherein R is a lower alkoxy group or a halogen atom and pharmaceutically acceptable salts thereof.

After an extensive research we have found that when a compound of the general formula (II):

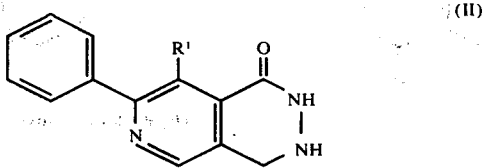

(wherein $R^1$ stands for a lower alkoxy group or a hydroxyl group) is halogenated to obtain a compound of the general formula (III):

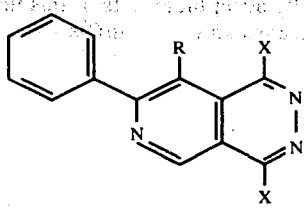

(wherein R has the same meaning as defined above and x is a halogen atom) and this latter compound is reacted with morpholine, there is obtained a pyrido[3,4-d]pyridazine derivative (I) and that the pyridazine derivatives (I) thus obtainable exhibit excellent diuretic properties.

Therefore, the main object of the present invention is to provide novel pyrido[3,4-d]pyridazines and their pharmaceutically acceptable salts which have excellent diuretic properties. Another object of the present invention is to provide an industrially feasible method for the production of such useful compounds.

Referring, now, to the above general formulas (I) and (III), the lower alkoxy group represented by R is methoxy or ethoxy. The halogen atom, also represented by R, may for example be chlorine or bromine. The lower alkoxy group represented by $R^1$ in general formula (II) is the same as R. X may for example be chlorine or bromine.

The pharmaceutically acceptable salts of the compound (I) include hydrochloric acid salt, hydrobromic acid salt sulfuric acid salt, nitric acid salt, phosphoric acid salt or the like.

The objective compounds of the present invention are produced by a method which comprises reacting a compound (II) with a halogenating agent to obtain a compound (III) and reacting a compound (III) with morpholine.

Thus, a compound (II) is halogenated to obtain a compound (III). This halogenation reaction is accomplished by permitting a halogenating agent to act upon a compound of general formula (II) in the presence or absence of a solvent.

As the halogenating agent, there may be mentioned for example, phosphorus pentahalides, e.g. phosphorus pentachloride, phosphorus pentabromide, etc.; phosphorus oxyhalides, e.g. phosphorus oxychloride, phosphorous oxybromide, etc., or suitable mixtures of such compounds. Commonly, the proportion of said halogenating agent is about 5 to 20 mole equivalents per mole of compound of general formula (II). When a reaction solvent is employed in this step, the solvent may be one that will not interfere with the reaction, such as hydrocarbons, e.g. benzene, toluene, hexane, etc.; ethers, e.g. diethylether, tetrahydrofuran, etc.; halogenated hydrocarbons, e.g. chloroform, dichloroethane, and so on. For the purpose of removing hydrogen halide that will be formed in the course of reaction, there may be incorporated in the reaction system a suitable basic reagent (e.g. a tertiary amine such as pyridine, trimethylamine, triethylamine, N,N-dimethylaniline or the like). While there is no particular restriction on the reaction temperature, the reaction is preferably conducted at room temperature up to about 130° C. The reaction time is normally about 2 to 5 hours. The resultant compound (III) can be isolated and purified by conventional procedures such as concentration, solvent extraction, pH adjustment, phase transfer, crystallization, recystallization and so on. Usually, however, the reaction mixture containing (III) can be used as a starting material in the subsequent reaction.

Then, the compound (III) is reacted with morpholine to obtain the desired product (I). While this reaction proceeds in the absence of a solvent, the progress of the reaction may be made smoother by means of an appropriate solvent. As the solvent for this reaction, use may be made, for example, of alcohols such as methanol, ethanol, etc., ethers such as tetrahydrofuran, ethyl ether, etc.; hydrocarbons and halogenated hydrocarbons such as benzene, chloroform, etc.; and esters such as ethyl acetate.

Morpholine is normally used in a proportion of about 2 to 4 mole equivalents per mole of starting compound of general formula (III) so that it may act also as the reaction solvent and acid acceptor. There are no special restrictions on the temperature, time and other conditions of reaction. Thus, while this reaction proceeds even at room temperature, it may be hastened by heating at temperatures up to the boiling point of the solvent used or of morpholine. The reaction time normally ranges from 1 to 5 hours, depending upon the particular starting material and solvent employed, for instance. The objective compound of general formula (I) thus obtained can be isolated and purified by conventional procedures such as extraction with an appropriate solvent (e.g. water, ethyl acetate, benzene, chloroform, ethanol, etc.), recrystallization, column chromatography and so on.

After the reaction, the reaction product is normally recovered from the reaction mixture in the form of a free base in accordance with conventional means such as concentration, crystallization, chromatography or the like. Of course, the reaction product of free basic form may be converted into the above-mentioned pharmaceutically acceptable salt by a per se known means.

The starting compound (II) for use according to this invention can be obtained, for example by subjecting a compound (IV) and N-substituted maleinimide to Diels Alder addition reaction, treating the resulting product compound (V) with an acid or base to obtain a compound (VI) and finally reacting the last-mentioned compound (VI) with hydrazine, as shown below in formulas.

Alternatively, as shown below in formulas, 8-hydroxy compound, i.e. the compound (II) wherein $R^1$ is hydroxy, can be obtained by reacting a starting material (VII) with hydrazine; and 8-lower alkoxy-compound i.e. the compound (II) wherein $R^1$ is a lower alkoxy group for example $CH_3O$ or $C_2H_5O$ can be obtained by the steps of reacting the compound (VII) with a lower alkyl halide and reacting the resulting 8-lower alkoxy-compound (VIII) further with hydrazine.

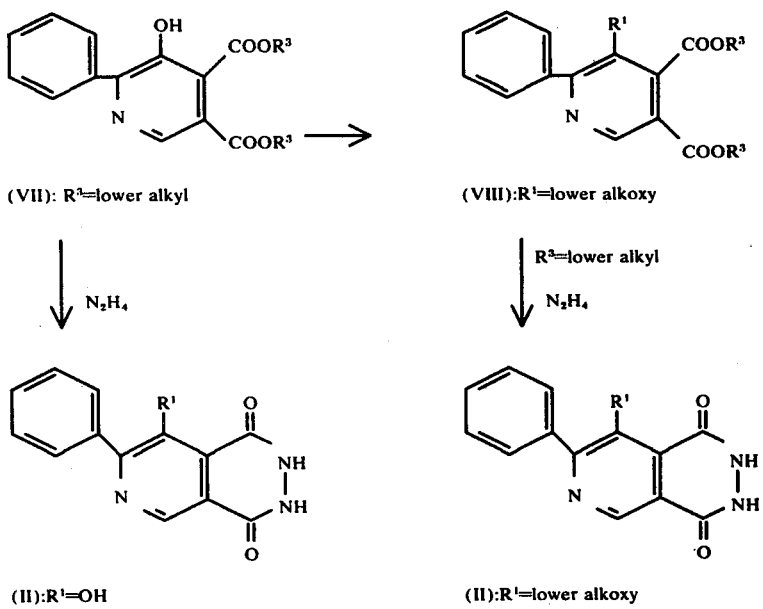

The compounds (I) and pharmaceutically acceptable salts thereof thus obtainable have eminent diuretic activity. Thus, the compound of general formula (I) wherein R is methoxy, for instance, displays highly enhanced diuretic action about three times as great as that of the comparable compound wherein R is a hydrogen atom. Therefore, the products (I) and their pharmaceutically acceptable salts of this invention are of value as diuretics and other drugs.

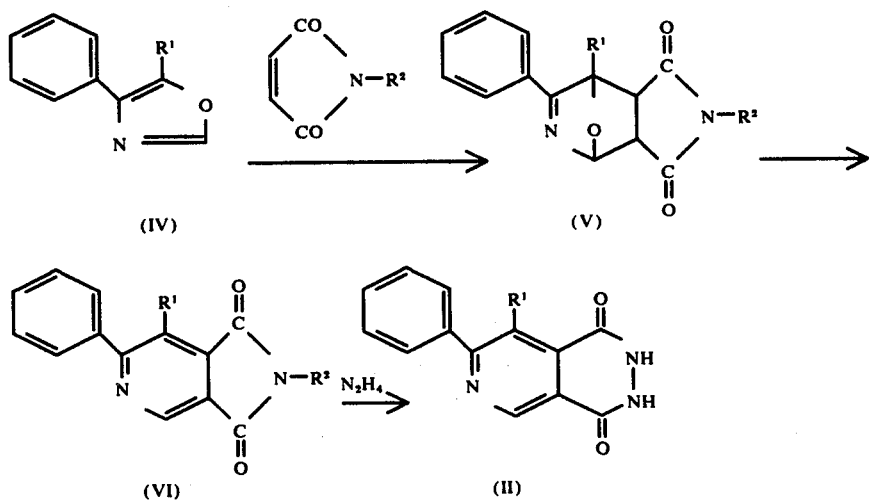

(wherein $R^1$ has the same meaning as defined hereinbefore; $R^2$ stands for an aliphatic or aromatic group).

The compounds (I) or their pharmaceutically acceptable salts can each be administered orally after they have been processed into tablets, capsules, powders.

granules, etc., by procedures known per se, along with conventional diluents or carriers. The compounds of the present invention is low toxic and can be well tolerated. The oral dosage of compound (I) or its salt is about 2 to 200 milligrams daily per adult human, preferably about 5 to 50 milligrams on the same basis, for the diuretic purpose for example in the therapy of edema and hypertension.

Pyrido[3,4-d]pyridazines having unexpectedly excellent diuretic activities include 8-methoxy-1,4-dimorpholino-7-phenylpyrido[3,4-d]pyridazine, 8-ethoxy-1,4-dimorpholino[3,4-d]pyridazine, 8-chloro-1,4-dimorpholino[3,4-d]-pyridazine and 8-bromo-1,4-dimorpholino[3,4-d]pyridazine.

REFERENCE EXAMPLE 1

A mixture of 5.0 g. 5-ethoxy-4-phenyloxazole and 4.8 g. N-phenylmaleimide was heated at 140° C for 4 hours. Then, it was dissolved by the addition of ethanol when hot and, after cooling, the resultant crystals were filtered off. The filtrate was concentrated to dryness and the residue was developed on column chromatography with a solvent mixture of acetone and benzene. The eluate at later stage was collected and the solvent was distilled off. The oily residue was dissolved in 100 ml of ethanol and, following the addition of 10 drops of concentrated hydrochloric acid, the solution was refluxed for 30 minutes. The ethanol was distilled off and chloroform was added to the residue, followed by cooling. The resultant crystals were recrystallized from ethyl acetate. The procedure provided 1.3 g. of 5-hydroxy-N,6-diphenylpyridine3,4-dicarboxamide as pale-yellow crystals melting at 225°–228° C.

Elemental analysis, for $C_{19}H_{12}O_3N_2$; Calculated: C, 72.14; H, 3.82; N, 8.86; Found: C, 71.95; H, 3.71; N, 8.52.

REFERENCE EXAMPLE 2

In 10 ml of dimethylformamide was dissolved 1 g. of 5-hydroxy-N,6-diphenylpyridine-3,4-dicarboximide, followed by the addition of 0.23 g. of 50% sodium hydride (oil). The mixture was stirred for 30 minutes, after which time 0.9 g. of methyl iodide was added, followed by 2 hours' stirring. The reaction mixture was poured in 50 ml of water, extracted with chloroform and washed with water. After drying, the solvent was distilled off and 5 ml of hydrazine hydrate was added. The mixture was heated at 120° for 1 hour. The excess hydrazine hydrate was distilled off under reduced pressure and the residue was diluted with water and made acid with acetic acid. The resultant crystals were collected by filtration, rinsed with water and dried.

The procedure provided 0.5 g. of 8-methoxy-7-phenylpyrido[3,4-d]pyridazine-1,4-(2H,3H)-dione, melting at 245°–250° C (decomposition).

Elemental analysis, for $C_{14}H_{11}O_3N_3$; Calculated: C, 62.45; H, 4.12; N, 15.61; Found: C, 62.07; H, 4.43; N, 15.74.

REFERENCE EXAMPLE 3

In 40 ml of dimethylformamide was dissolved 4.2 g. of ethyl 5-hydroxy-6-phenylpyridine-3,4-dicarboxylate. hydrochloride and while the solution was cooled with ice and stirred, 1.4 g. of 50% sodium hydride (oil) was added. After 30 minutes, 5 ml of methyl iodide was added and the mixture was further stirred for 1 hour. The reaction mixture was poured in 300 ml of water, made alkaline with 10% sodium hydroxide and extracted with benzene. The extract was dried and distilled free of the solvent and the residue was dissolved in ether. Following the addition of alcoholic hydrochloric acid, the solution was cooled and the resultant crystals were recystallized from a mixture of benzene and ether. The procedure provided 2.8 g. of ethyl-5-methoxy-6-phenylpyridine-3,4-dicarboxylate. hydrochloride, melting at 86°–98° C.

Elemental analysis, for $C_{18}H_{20}O_5O_5NCl$; Calculated: C, 59.10; H, 5.51; N, 3.83; Found: C, 59.09; H, 5.26; N, 3.85.

REFERENCE EXAMPLE 4

A mixture of 1.5 g. ethyl 5-methoxy-6-phenyl-pyridine3,4-dicarboxylate·hydrochloride, 30 ml ethanol and 3 ml hydrazine hydrate was refluxed for 4 hours. After cooling, the yellow crystals were recovered by filtration, suspended in 15 ml of water, made acid with acetic acid and stirred for 1 hour. The crystals were collected by filtration, rinsed with water and dried. The procedure provided 0.7 g. of 8-methoxy-7-phenylpyrido[3,4-d]pyridazine-1,4(2H,3H)-dione as pale yellow microgranular crystals melting at 245°–250° C (decomposition).

REFERENCE EXAMPLE 5

A mixture of 2 g. ethyl 5-hydroxy-6-phenyl-pyridine3,4-dicarboxylate·hydrochloride, 40 ml ethanol and 4 ml hydrazine hydrate was refluxed for 4 hours. After cooling, the pale yellow crystals were recovered by filtration, suspended in 20 ml of water and made acid with dilute hydrochloric acid. The crystals were recovered by filtration, rinsed with water and dried. The procedure provided 1.2 g of 8-hydroxy-7-phenylpyrido[3,4-d]pyridazine-1,4-(2H,3H)-dione, melting point: more than 300° C.

Elemental analysis, for $C_{13}H_9O_3N_3$; Calculated C, 61.17; H, 3.55; N, 16.47; Found: C, 61.01; H, 3.23; N, 16.22.

EXAMPLE 1

A mixture of 0.5 g. 8-methoxy-7-phenylpyrido[3,4-d]-pyridazine-1,4(2H,3H)-dione, 7.5 ml phosphorus oxychloride and 0.33 ml α-picoline was heated at 100° C for 3 hours. The phosphorus oxychloride was distilled off under reduced pressure, and ice-water was added to the residue. The resultant crystals were collected by filtration. To the crystals was added 8 ml of morpholine and the mixture was heated at 130° C for 1 hour. The excess morpholine was distilled off under reduced pressure and water was added to the residue. The resultant crystals were recovered by filtration and recrystallized from methanol. The procedure provided 0.4 g. of 8-methoxy-1,4-dimorpholino7-phenyl-pyrido[3,4-d]pyridazine as yellow needles melting at 182°–188° C.

Elemental analysis, for $C_{22}H_{25}O_3N_5$; Calculated: C, 64.85; H, 6.18; N, 17.19; Found: C, 64.62; H, 5.97; N, 16.88.

EXAMPLE 2

A mixture of 0.4 g. 8-hydroxy-7-phenylpyrido[3,4-d]-pyridazine-1,4(2H,3H)-dione, 6 ml phosphorus oxychloride and 0.4 ml α-picoline was heated at 120° C for 8 hours. The phosphorus oxychloride was distilled off under reduced pressure and ice-water was added to the residue. The resultant crystals were recovered by filtration and 8 ml of morpholine was added. The mixture was heated at 140° C for 3 hours. The excess morpholine was distilled off under reduced pressure and water was added to the residue. The crystals that had separated were recovered by filtration, purified by column chromatography on silica gel and recrystallized from ethanol. The procedure provided 0.2 g. of 8-chloro-1,4-dimorpholino-7-phenylpyrido[3,4-d]pyridazine as yellow needles melting at 201°–204° C.

Elemental analysis, for $C_{21}H_{22}O_2N_5Cl$; Calculated; C, 61.23; H, 5.38; N, 17.00; Found: C, 60.92; H, 5.34; N, 16.79.

What is claimed is:

1. 8-methoxy-1,4-dimorpholino-7-phenylpyrido[3,4-d]-pyridazine or a pharmaceutically acceptable salt thereof.

* * * * *